United States Patent [19]

Miller

[11] Patent Number: 4,763,077

[45] Date of Patent: Aug. 9, 1988

[54] SENSOR CIRCUIT RESPONSIVE TO DIFFERENT FLUID CONDUCTIVITIES

[75] Inventor: Francis M. Miller, Clearwater, Fla.

[73] Assignee: Conax Florida Corporation, St. Petersburg, Fla.

[21] Appl. No.: 922,074

[22] Filed: Oct. 20, 1986

[51] Int. Cl.$^4$ ............................................. G01N 27/02
[52] U.S. Cl. .................................... 324/439; 361/251; 340/620
[58] Field of Search ............... 324/438, 439, 446, 450; 24/603; 340/620; 361/251

[56] References Cited

U.S. PATENT DOCUMENTS

| | | | |
|---|---|---|---|
| 4,024,440 | 5/1977 | Miller | 361/251 |
| 4,041,865 | 8/1977 | Evans et al. | 361/251 X |
| 4,165,509 | 8/1979 | Betts et al. | 340/620 |
| 4,263,587 | 4/1981 | John | 340/620 |
| 4,318,041 | 3/1982 | Fredericks | 324/450 X |
| 4,382,231 | 5/1983 | Miller | 324/439 |
| 4,389,889 | 6/1983 | Larson | 340/620 X |
| 4,513,248 | 4/1985 | Miller | 324/439 |
| 4,589,172 | 5/1986 | Hoenigs et al. | 24/603 X |

Primary Examiner—M. H. Paschall
Assistant Examiner—A. Jonathan Wysocki
Attorney, Agent, or Firm—Christel, Bean & Linihan

[57] ABSTRACT

A circuit for operating a load in response to predetermined external conductivity conditions including a pair of sensing electrodes, a source of electrical energy connected to one of the electrodes, a load, an operating circuit connected to the load, to the source and to the other of the sensing electrodes and including a first portion for storing electrical energy for operating the load and a second portion utilizing the stored energy to operate the load, and a control for allowing operation of only the first circuit portion when the sensing electrodes are exposed to a first medium having a predetermined electrical conductivity and then allowing operation of the second portion thereafter and when the sensing electrodes are exposed to a second medium having a different electrical conductivity. The control and its connection in the circuit are determined so as to be responsive to the first medium being of higher electrical conductivity than the second medium, for example water being the first medium and air the second. The load can be an electro-explosive device of an automatic release mechanism for an aviator helmet.

15 Claims, 1 Drawing Sheet

SENSOR CIRCUIT RESPONSIVE TO DIFFERENT FLUID CONDUCTIVITIES

BACKGROUND OF THE INVENTION

This invention relates to circuits for controlled charging and discharging of energy storage devices such as capacitors associated with a load, and more particulary to a new and improved circuit for controlled charging and discharging of an energy storage device in response to predetermined fluid conductivity conditions.

One area of use of the present invention is in controlled firing of electro-explosive devices, although the principles of the invention can be variously applied. Electro-explosive devices can find use in a variety of applications, for example parachute canopy release mechanisms, pressurized gas release devices for inflating floatation equipment such a life vests or life rafts, and many other applications. A typical circuit for activating an electro-explosive device includes a capacitor which is charged from a supply and then discharged in a controlled manner through the device. The circuit also includes sensing electrodes and a conductivity sensing portion whereby the controlled charging and discharging of the capacitor typically has been performed only when the sensing electrodes are exposed to liquid having a predetermined electrical conductivity, i.e. a body of water.

In accordance with the present invention it would be desirable to provide such a circuit wherein the controlled charging and discharging of the energy storage device or capacitor is in response to the sensing electrodes being exposed sequentially to mediums of different conductivity. In particular, the capacitor could be charged when the electrodes are exposed to a body of water and subsequently discharged when the electrodes leave the water and are exposed to air. One example of use is firing an electro-explosive device in a pressurized gas release device for inflating a floatation equipment in the form of life vests. When a helicopter enters water it usually inverts, and to prevent drowning the lift vest worn by the pilot should not be automatically inflated until he is able to leave the submerged helicopter and rise to the surface of the water. When ship personnel wearing life vests work below deck and a large volume of water suddenly enters the area, it is desired not to have the vests inflated so that they can more easily climb ladders or stairs in leaving the area. Another example is firing an electro-explosive device in an aviator helmet breathing mask release mechanism. It is desired not to release the mask while the pilot is under water after ejection and descent by parachute thereby utilizing the small residual air supply in the breathing mask and tube. However, once the pilot's head emerges above the water surface, it is desired to remove the mask especially since the pilot may be unconscious and drown if the mask is not removed.

SUMMARY OF THE INVENTION

It is, therefore, a primary object of this invention to provide a new and improved circuit for controlled charging and discharging of energy storage devices such as capacitors associated with a load.

It is a more particular object of this invention to provide such a circuit wherein controlled charging and discharging of energy storage devices is in response to sequential exposure to mediums or fluids of different electrical conductivity.

It is a further object of this invention to provide such a circuit wherein charging of the energy storage device is in response to exposure to water and discharging thereof is in response to exposure to air.

It is a further object of this invention to provide such a circuit for firing an electro-explosive device.

It is a further object of this invention to provide such a circuit for firing an electro-explosive device of an automatic release mechanism for an aviator helmet.

The present invention provides a circuit for operating a load in response to predetermined external conductivity conditions comprising a pair of sensing electrodes, a source of electrical energy connected to one of the electrodes, a load, an operating circuit connected to the load, to the source and to the other of the sensing electrodes and including a first portion for storing electrical energy for operating the load and a second portion utilizing the stored energy to operate the load, and control means for allowing operation of only the first circuit portion when the sensing electrodes are exposed to a first medium having a predetermined electrical conductivity and then allowing operation of the second portion thereafter and when the sensing electrodes are exposed to a second medium having a different electrical conductivity. The control means and its connection in the circuit are determined so as to be responsive to the first medium being of higher electrical conductivity than the second medium, for example water being the first medium and air the second. The load can be an electro-explosive device of an automatic release mechanism for an aviator helmet.

In particular, the source can comprise a battery having one terminal connected to one of the sensing electrodes, and the circuit can include a first branch comprising the series combination of resistance means and semiconductor unidirectional current conducting means in the form of a diode, the resistance means being connected to the other terminal of the battery, and the junction of the resistance means and diode being connected to the other of the sensing electrodes. A second branch is connected across the first branch and comprises the series combination of the load, for example electro-explosive device, and a controlled semiconductor switch, the control terminal of which is connected to the junction of the resistance means and diode. A third branch comprising the energy storage means or capacitor is connected across the second branch.

In response to the sensing electrodes being exposed to a medium of predetermined electrical conductivity such as water, a circuit is completed including the electrodes, the battery, the capacitor and the diode so as to store energy in the capacitor while at the same time maintaining the controlled semiconductor swich open, and in response to the sensing electrodes being exposed to an essentially non-conductive medium such as air the battery is functionally removed from the circuit branches and the capacitor initially creates a potential on the resistance means which is applied to the control terminal of the switch closing the same thereby completing a discharge circuit for the capacitor through the load, i.e. firing the electro-explosive device.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is a side elevational view illustrating use of the circuit of the present invention in an automatic release mechanism for an aviator helmet; and FIG. 2 is a schematic diagram of the circuit of the present invention for operating a load in response to predetermined external conductivity conditions.

DETAILED DESCRIPTION OF THE ILLUSTRATED EMBODIMENT

Figure 1:
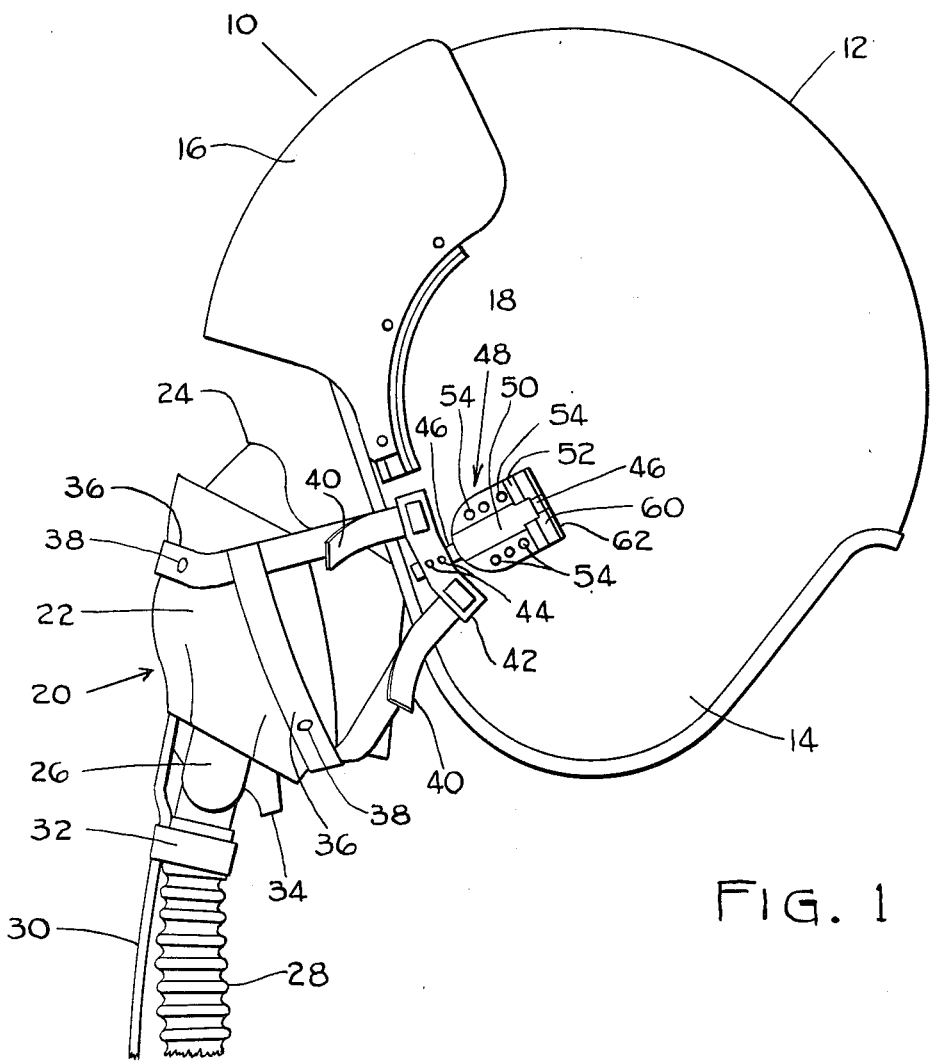

FIG. 1 illustrates one example of use of the circuit of the present invention for firing an electro-explosive device in an automatic release mechanism for an aviator helmet breathing mask. An aviator helmet generally designated 10 comprises a shell 12, an ear cover portion 14 on each side and a cover 16 for a visor (not shown) movable on a track 18 to and from a retracted position beneath the cover 16. A breathing mask generally designated 20 comprises a body 22 shaped to fit over the mouth and nose of the aviator's face including a nosepiece or formation 24 in the upper region of body 22 as viewed in FIG. 1 and an inlet formation 26 in the lower region thereof. Inlet 26, in turn, is in fluid communication with one end of a hose 28 for supplying breathing gas to the interior of mask 20. Normally, hose 28 is connected at the other end to a source of breathing gas such as a tank. When the pilot is ejected from the aircraft during an emergency, the end of hose 28 is disconnected from the tank, and the length of hose 28 remains connected at the other end to maks 20 and travels with the pilot as he descends by parachute. A cable 30 connected to hose 28 by a clamp 32 leads at one end into mask 20 and comprises a plurality of conductors for electrical connection to a microphone (not shown) in mask 20 and earphone (not shown) in helmet 10. The other end of cable 30 normally is connected to communications equipment in the aircraft and is disconnected therefrom when the pilot ejects and travels with him during descent by parachute. The mask also includes an exhaust outlet 34 in the lower portion thereof and provided with a check valve (not shown) through which the pilot expels air.

Mask 20 is releasably connected to helmet 10 in the following manner. Mask body 22 is received in a harness comprising straps 36 which are secured to body 22 by fasteners 38. On each side of the mask, the straps terminate in two free ends 40 which are looped or otherwise connected in corresponding slots near opposite ends of a transverse arm or bar 42. Arm 42, in turn, is connected by suitable fasteners 44 substantially midway thereof to one end of a bayonet finger or connector 46, the other end of which is releasably engaged in a retaining device 48 mounted on the exterior surface of helmet shell 12 near the front and upwardly of the ear covering portion 14. On the opposite side of mask 20 and helmet 10 (not shown) there is provided a similar arrangement of strap ends connected in a transverse bar secured to a bayonet finger engaged in a retaining device mounted on the exterior surface of helmet shell 12.

The retaining device 48 on one side of helmet 10 is provided with an electro-explosive devide for automatically releasing bayonet finger 46 for removal of mask 20 from the pilot's face, and the electro-explosive device is operated by the circuit of the present invention. This is to prevent drowning after the ejected pilot has landed by parachute into water. The structure of retaining devcie 48 and the portion of bayonet finger 46 received therein can have various forms. The illustrative retaining device 48 shown in FIG. 2 comprises an outer cover plate 50, a pair of jaw members (not shown) in spaced relation behind plate 50 as viewed in FIG. 1 and defining therebetween an elongated passage for receiving bayonet finger 46, and an actuator housing 52 behind the jaws and mounted to shell 12 by suitable means. Spring wire elements extending longitudinally along opposite sides of finger 46 snap into recesses between adjacent teeth of the jaws. Housing 52 contains an electro-explosive device, a chamber for receiving gas upon explosive ignition of the device and a piston in the chamber and positioned to act forcibly against bayonet finger 46. Upon ignition of the device to explosively release gas, the piston is forced outwardly as viewed in FIG. 1 which in turn forces bayonet finger 46 outwardly against plate 50 shearing fastening screws 54 which hold plate 50 in the mechanism thereby releasing finger 46 from device 48 and removing mask 20 from the pilot's face. In particular, bayonet 46 falls downwardly as viewed in FIG. 1 allowing mask 20 to swing away and to one side of helmet 10.

The circuit of the present invention is contained in a body 60 of insulative material located adjacent one end of actuator housing 52 as shown in FIG. 1. A sensor element 62 is located adjacent the end of body 60. Element 62 can be in the form of a thin plate of plastic or like insulative material provided with a recess in the exposed face to accommodate an electrode of metal such as stainless steel or aluminum. The conductive surface or portion of either actuator housing 52 or mounting plate 50 can comprise the other sensing electrode as will be described.

Figure 2:
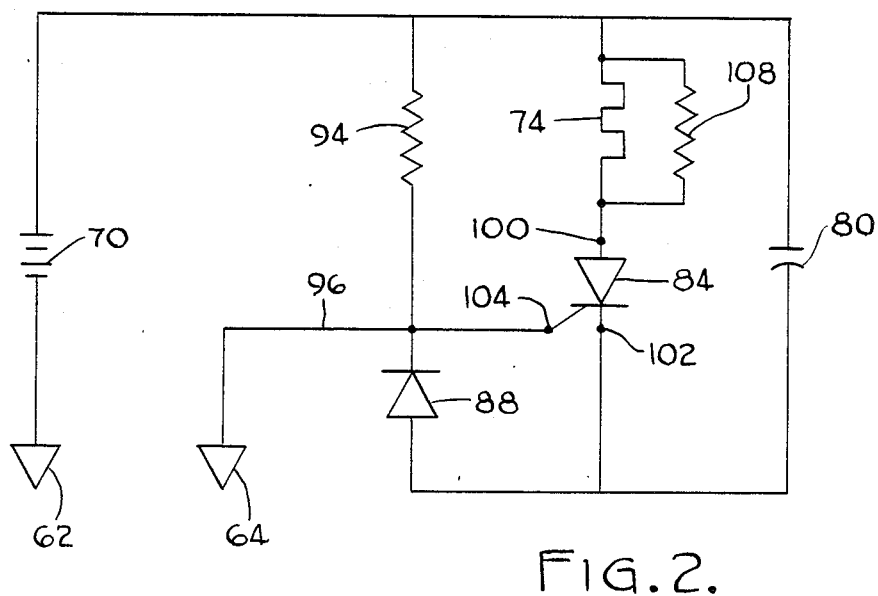

The circuit of the present invention is shown in FIG. 2 and includes sensing means in the form of a pair of sensing electrodes 62 and 64 and a source of electrical energy in the form of battery 70 connected to one of the electrodes. In the circuit shown, electrode 62 is connected to the negative terminal of battery 70. The circuit further includes a load 74 which in the present example is in the form of an electro-explosive device or bridgewire. There is also provided an operating circuit connected to load 74, to source 70 and to the other electrode 64 which includes a first portion including a capacitor 80 for storing electrical energy for operating load 74 and a second portion including a controlled switch 84 utilizing the stored energy to operate load 74. There is also provided control means including a diode 88 for allowing operation of only the first circuit portion when sensing electrodes 62,64 are exposed to a first medium having a predetermined electrical conductivity and then allowing operation of the second portion thereafter and when the sensing elecrodes 62,64 are exposed to a second medium having a different electrical conductivity. In the circuit of the present illustration the nature of the control means and its connection in the circuit are such that it is responsive to the first medium being of higher electrical conductivity than the second medium, in particular the first medium being water and the second medium being air.

Referring to the circuit of FIG. 2 in further detail, it includes a first branch comprising the series combination of resistance means in the form of voltage-droping resistor 94 and semiconductor unidirectional current conducting means in the form of diode 88. In the circuit shown, one terminal of resistor 94 is connected to the positive terminal of battery 70 and the other terminal of resistor 94 is connected to the cathode of diode 88. Sensing electrode 64 is connected by line 96 to the junction of resistor 94 and diode 88.

The circuit includes a second branch connected across the first branch and comprising the series combination of load 74 and semiconductor switching means or controlled switch 84 having anode, cathode and control terminals 100,102 and 104, respectively. One terminal of the electro-explosive device or bridgewire 74 is connected to the terminal of resistor 94 which is connected to battery 70, and the other terminal of device 74 is connected to the anode terminal 100 of controlled switch 84. The cathode terminal 102 of controlled switch 84 is connected to the anode of diode 88, and the control terminal 104 of controlled switch 84 is connected to the cathode of diode 88. A protective resistor 108 is connected across electro-explosive device 74 for a purpose to be described.

The circuit includes a third branch connected across the second branch and comprising the energy storage means in the form of capacitor 80. One terminal of capacitor 80 is connected to the junction of load 74 and resistor 94, and the other terminal of capacitor 80 is connected to cathode terminal 102 of controlled switch 84.

In response to sensing electrodes 62,64 being exposed to a medium or fluid of predetermined conductivity, for example water, a circuit is completed including electrodes 62,64, source 70, energy storage means 80 and the unidirectional current conducting means or diode 88 so as to store energy in the storage means 80 while at the same time maintaining switching means 84 open. Then in response to electrodes 62,64 being exposed to an essentially non-conductive medium or fluid such as air, source 70 is functionally removed from the circuit branches and energy storage means 80 initially creates a potential on resistance means 94 which is applied to control terminal 104 causing switching means 84 to close thereby completing a discharge circuit for the energy storage means 80 through the load 74.

In particular, when electrodes 62,64 are immersed in water a charging circuit is completed through diode 88 and the firing capacitor 80, charging the latter to a potential approaching that of the source 70. The higher the value of resistor 94, the more closely the voltage across firing capacitor 80 will approach the voltage of source 70. The firing circuit through primer bridge wire 74 includes the normally open controlled switch 84 which is a silicon-controlled rectifier.

Upon immersion of electrodes 62,64 in water, there is a potential of approximately 0.5 volts across diode 88, driving gate 104 of SCR 84 negative relative to cathode 102. Diode 88 causes the gate/cathode junction to be reverse biased, when sensors 62,64 are in water, and the firing circuit through primer 74 therefore remains open as firing capacitor 80 is charged. The arrangement is such that gate 104 could be at equal potential to that of cathode 102 without turning on SCR 84.

When electrodes 62,64 are removed from the water medium and are in air, the battery 70 is functionally removed from the circuit, and the firing capacitor 80 becomes the power source. This reverses the polarity of the gate/cathode of SCR 84 with current initially passing through resistor 94, driving gate 104 positive relative to cathode 102 whereup controlled switch 84 closes, completing the firing circuit through primer bridge wire 74 which has a resistance significantly lower than that of resistor 94. Thus, resistor 94 provides a path from firing capacitor 80 to allow the gate/cathode junction of controlled switch 84 to become forward biased, turing the switch 84 on and completing the firing circuit through the primer 74.

The lower the resistance between electrodes 62,64 the higher the voltage across resistor 94, and the rate of charge of firing capacitor 80 depends upon the resistance of the water medium in which the electrodes are placed. The sensitivity of the circuit can be adjusted by changing the value of resistance 94. In this connection, resistance 94 in conjunction with the resistance of the medium across electrodes 62,64 functions as a voltage divider whereby the higher the value of resistance 94 the greater the voltage will be across capacitor 80. Resistor 108 prevents a voltage build-up across the circuit connections to electro-explosive device 74 when the device is removed during replacement or repair. Otherwise, if such build-up were allowed to occur, re-connection of device 74 could operate controlled rectifier 84 causing inadvertent firing of device 74.

Thus, the foregoing operation could be summarized as the controlled charging and discharging of the energy storage device or capacitor 80 in response to the sensing electrodes 62,64 being exposed sequentially to mediums or fluids of different electrical conductivity, in particular the capacitor 80 being charged when electrodes 62,64 are exposed to a body of water and subsequently being discharged when the electrodes 62,64 leave the water and are exposed to air. In terms of operating or firing the electro-explosive device 74, the circuit arms when electrodes 62,64 are immersed in a body of water and the circuit fires when electrodes 62,64 leave the water.

When the circuit of the present invention is employed in an automatic release mechanism for an aviator helmet breathing mask as illustrated in FIG. 1, the circuit arms, i.e. capacitor 80 is charged, when the pilot's head and thus helmet 10 goes under water upon parachute descent into the water, and capacitor 80 remains charged for as long as the pilot's head is under water which normally is a few seconds. Then, when the pilot floats upwardly to the surface of the water and his head emerges from the water, electrodes 62,64 are exposed to the air causing discharge of capacitor 80 through electro-explosive device 74 to fire the same and release mask 20 from the helmet 10 and from the pilot's face as previously described. This prevents drowning because if the pilot is unconscious, with mask 20 covering his face and the free end of hose 28 in the water, there would be no air for the pilot to breathe.

By way of example, in an illustrative circuit for use in the foregoing mask release mechanism electrode 62 is of stainless steel, electrode 64 is of aluminum, source 70 is a 6 volt battery, resistor 94 has a value of about 1 megohm, diode 88 is type 1N914, load 74 is an electro-explosive device commercially available from Conax Florida Corporation model CC-114 rated 2–5 ohms, resistor 108 has a magnitude of about 1 kilohm, switch 84 is a 2N5060 silicon controlled rectifier having a gating voltage from about 0.4 volts to about 0.8 volt, and capacitor 80 has a magnitude of about 47 microfarads.

It is therefore apparent that the present invention accomplishes its intended objects. While an embodiment of the present invention has been described in detail, that is for the purpose of illustration, not limitation.

I claim:

1. A circuit for operating a load in response to predetermined external conductivity conditions comprising:
   (a) a pair of sensing electrodes;
   (b) a source of electrical energy connected to one of said electrodes;
   (c) a load;
   (d) an operating circuit connected to said load, to said source and to the other of said sensing electrodes, said circuit including a first portion having means for storing electrical energy for operating said load and a second portion including a controlled switch connected to said load for providing a path enabling said stored energy to operate said load; and
   (e) said circuit further including control means for allowing operation of only said first circuit portion when said sensing electrodes are exposed to a first medium having a predetermined electrical conductivity and then allowing operation of said second portion thereafter and when said sensing electrodes are exposed to a second medium having a different electrical conductivity.

2. A circuit according to claim 1, wherein the nature of said control means and its connection in said circuit are determined so as to be responsive to said first medium being of higher electrical conductivity than said second medium.

3. A circuit according to claim 1, wherein the nature of said control means and its connection in said circuit are determined to be responsive to said first medium being water and said second medium being air.

4. A circuit according to claim 1, wherein said first portion of said operating circuit includes a capacitor and said second portion of said operating circuit includes a controlled switch in series with said load and defining a discharge path for said capacitor through said load, said switch being connected in controlled relation to said control means whereby said switch is open during storing of electrical energy in said capacitor and is closed for operation of said load.

5. A circuit according to claim 1, wherein said control means comprises a diode connected in said circuit so as to conduct when said electrodes are exposed to a conductive medium and allow operation of only said first circuit portion by defining a path for storing energy and so as to open when said electrodes are exposed to a non-conductive medium to discontinue operation of said first portion and allow operation of said second circuit portion.

6. A circuit according to claim 1, wherein said load is an electro-explosive device.

7. A circuit according to claim 1, wherein said load is an electro-explosive device in an automatic release mechanism for an aviator helmet breathing mask.

8. A circuit according to claim 1 wherein said first portion of said operating circuit includes a capacitor, wherein said second portion of said operating circuit includes a controlled switch in series with said load and defining a discharge path for said capacitor through said load, said switch being connected in controlled relation to said control means whereby said switch is open during storing of electrical energy in said capacitor and is closed for operation of said load, and wherein said control means comprises a diode connected in said circuit so as to conduct when said electrodes are exposed to a conductive medium and allow operation of only said first circuit portion by defining a path for charging said capacitor and so as to open when said electrodes are exposed to a non-conductive medium to discontinue charging of said capacitor and to close said switch to discharge said capacitor through said load.

9. A circuit for operating a load in response to predetermined external conductivity conditions comprising:
   (a) a pair of sensing electrodes;
   (b) a source of electrical energy having a pair of terminals, one of which is connected to one of said electrodes;
   (c) a first branch comprising the series combination os resistance means and semiconductor unidirectional current conducting means, said resistance means being connected to the other terminal of said source and the junction of said resistance means and said unidirectional current conducting means being connected to the other of said electrodes;
   (d) a second branch connected across said first branch and comprising the series combination of a load and semiconductor switching means having anode, cathode and control terminals, said control terminal being connected to the junction of said resistance means and said unidirectional current conducting means; and
   (e) a third branch comprising energy storage means connected acorss said second branch;
   (f) whereby in response to said sensing electrodes being exposed to a medium of predetermined electrical conductivity a circuit is completed including said electrodes, said source, said energy storage means and said unidirectional current conducting means so as to store energy in said storage means while at the same time maintaining said switching means open and in response to said sensing means being exposed to an essentially non-conductive medium said source is functionally removed from said circuit branches and said energy storage means initially creates a potential on said resistnace means which is applied to said control terminal causing said switching means to close thereby completeing a discharge circuit for said energy storage means through said load.

10. A circuit according to claim 9, wherein said unidirectional current conducting means comprises a diode, the cathode of which is connected to said resistance means.

11. A circuit according to claim 9, wherein the anode of said switching means is connected to said load.

12. A circuit according to claim 9, wherein said unidirectional current conducting means comprises a diode, the cathode of which is connected to said resistance means, and wherein the anode of said switching means is connected to said load and the cathode of which is connected to the anode of said diode.

13. A circuit according to claim 9, wherein said energy storage means comprises a capacitor connected across the series combination of said load and said switching means.

14. A circuit according to claim 9, wherein said load comprises an electro-explosive device.

15. A circuit according to claim 9, wherein said load is an electro-explosive device in an automatic release mechanism for an aviator helmet breathing mask.

* * * * *

UNITED STATES PATENT AND TRADEMARK OFFICE
CERTIFICATE OF CORRECTION

PATENT NO. : 4,763,077
DATED : August 9, 1988
INVENTOR(S) : Francis M. Miller

It is certified that error appears in the above-identified patent and that said Letters Patent are hereby corrected as shown below:

<u>In Claim 9</u>

Part (c), line 1, "os" should be --of--.

Part (f), line 12, "resistnace" should be --resistance-- and on line 14, "completeing" should be --completing--.

Signed and Sealed this

Thirteenth Day of December, 1988

Attest:

DONALD J. QUIGG

*Attesting Officer*   *Commissioner of Patents and Trademarks*